US006391174B1

(12) United States Patent
Rowe et al.

(10) Patent No.: US 6,391,174 B1
(45) Date of Patent: May 21, 2002

(54) ION EXCHANGE MEMBRANE FOR DISSOLVED GAS SENSOR

(75) Inventors: Robert D. Rowe; Thomas M. Fyles; George D. Robertson, all of Victoria (CA)

(73) Assignee: RhoCraft Research and Development Ltd., Victoria (CA)

( * ) Notice: Subject to any disclaimer, the term of this patent is extended or adjusted under 35 U.S.C. 154(b) by 0 days.

(21) Appl. No.: 09/444,867

(22) Filed: Nov. 22, 1999

Related U.S. Application Data
(60) Provisional application No. 60/109,431, filed on Nov. 23, 1998.

(51) Int. Cl.[7] .............................................. G01N 27/333
(52) U.S. Cl ....................... 204/417; 204/415; 204/416; 204/418
(58) Field of Search ................................. 204/415, 418, 204/416, 417, 419

(56) References Cited

U.S. PATENT DOCUMENTS

| | | | | |
|---|---|---|---|---|
| 3,448,032 A | * | 6/1969 | Settzo et al. |
| 4,224,114 A | * | 9/1980 | Fiedler-Linnersund et al. |
| 4,314,895 A | * | 2/1982 | Spaziani et al. |
| 4,409,980 A | * | 10/1983 | Yano et al. |
| 4,534,356 A | * | 8/1985 | Papadakis |
| 4,933,048 A | * | 6/1990 | Lauks |
| 5,212,050 A | * | 5/1993 | Mier et al. |
| 5,906,719 A | * | 5/1999 | Treloar et al. |

* cited by examiner

Primary Examiner—T. Tung
(74) Attorney, Agent, or Firm—Klarquist Sparkman, LLP

(57) ABSTRACT

An ion exchange membrane for use in sensors which measure dissolved gases. Disclosed is a method for using ion exchangers in gas permeable membranes to maintain optimal conditions in the electrolyte contained within the sensor. This can greatly extend the lifetime and improve the stability relative to sensors of similar size and electrolyte volume that have been constructed using prior art.

21 Claims, 1 Drawing Sheet

Example of the invention as it applies to a dissolved oxygen sensor

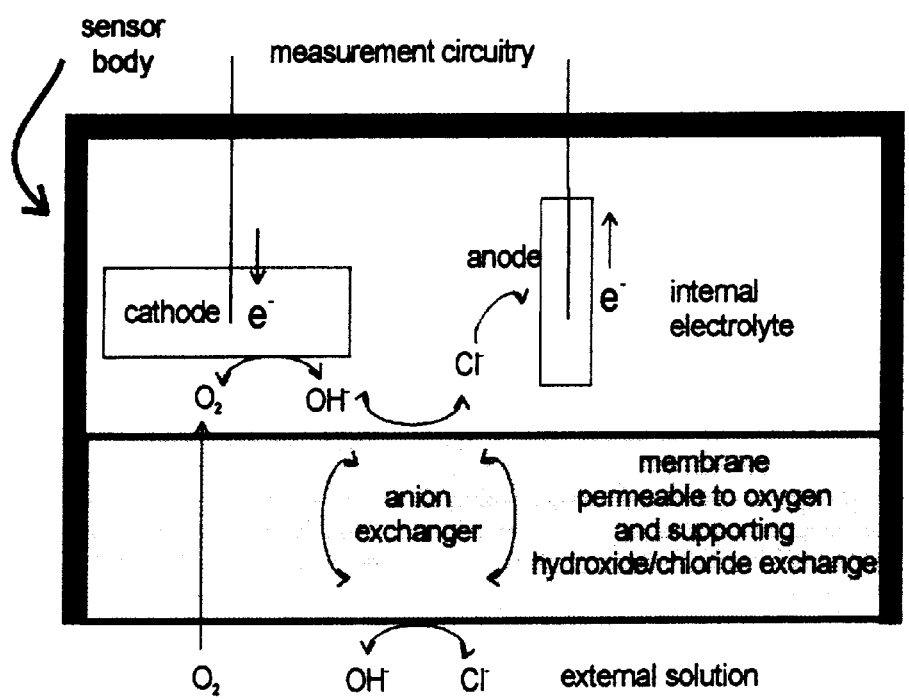
Figure 1: Example of the invention as it applies to a dissolved oxygen sensor

US 6,391,174 B1

ION EXCHANGE MEMBRANE FOR DISSOLVED GAS SENSOR

CROSS-REFERENCE TO RELATED APPLICATIONS

This application claims benefit of provisional application Ser. No. 60/109,431 filed Nov. 23, 1998.

US Patents

U.S. Pat. No. 4,933,048 Lauks Application No. 156262 Filed Feb. 16, 1988

U.S. Pat. No. 5,212,050 Meir, et al. Application No. 568441 Filed Aug. 15,1990

U.S. Pat. No. 4,534,356 Papadakis Application No. 403, 808 Filed Jul. 30, 1982

U.S. Pat. No. 4,409,980 Yano et al. Application No. 293304 Filed Aug. 17, 1981

European Patents

EP0496521 Tsukada et al. Application No, EP19920300305 19920114

Other References Cited

Janata, J. Principles of Chemical Sensors, Plenum Publishing, 1991, Chapter 4; Polarographic Oxygen Sensors Gnaiger, E, and Forstner, H. (eds.) Springer-Verlag, Kesting, R. Synthetic Polymer Membranes, $2^{nd}$ Ed, Wiley-Interscience, 1985 Ion Exchange Processes: Advances and Applications, A. Dyer, M. J. Hudson, P. A. Williams.(Eds.) Royal Society of Chemistry, 1993

Liquid Membranes: Theory and applications, Noble, R. D and Way, J. D (Eds.) ACS Symposium Series 347, American Chemical Society, 1987

STATEMENT REGARDING FEDERALLY SPONSORED RESEARCH OR DEVELOPMENT

Not Applicable.

REFERENCE TO MICROFICHE

Not Applicable.

BACKGROUND OF INVENTION

This invention relates to the measurement of dissolved gases in liquid samples by means of an amperometric sensor. Such sensors, known collectively as Clark cells, have been extensively described (Janata, J. Principles of Chemical Sensors, Plenum Publishing, 1991, Chapter 4; Polarographic Oxygen Sensors Gnaiger, E, and Forstner, H. (eds.) Springer-Verlag, 1983) and are widely used for the analysis of gases which are readily reduced or oxidized such as hydrogen sulfide, NO, CO, or oxygen. Clark cells consist of a gas permeable membrane enclosing an electrolyte in contact with a working and reference electrode. The gas crosses the membrane by diffusion, and is reduced or oxidized at the working electrode thereby creating a current flow. The stability and reliability of Clark cells depends on many factors. Of importance to this invention is the limitation on sensor lifetime imposed by the amount of electrolyte within the Clark cell. Since the oxidation and reduction processes consume components of the electrolyte, Clark cells are inherently prone to instability and limited lifetime due to the exhaustion of the electrolyte. This problem is particularly acute for small electrodes (microelectrodes). There have been many attempts in the past to address this shortcoming through mechanical means, for example European Patent No. EP0496521 proposes such a method. In addition, Clark cells are expensive to construct and require frequent maintenance and calibration.

BRIEF SUMMARY OF INVENTION

A practitioner skilled in the art will recognize that exhaustion of the electrolyte is a serious barrier to the construction of long lived and stable Clark cells. The invention describes a membrane with a combination of properties: selective permeability for the gas to be analyzed and an ion exchange capacity to allow discharge of the ionic byproducts of the redox reaction. A membrane formed in this manner will allow an amperometric sensor to function in a stable manner for a much longer period of time than a sensor that must rely on only the ions present in the original electrolyte volume. This in turn will allow someone skilled in the art to produce a very small AND long lived, stable sensor.

Ion exchangers for both cations and anions are well-known, either formulated as a functionalized polymer membrane (see for example Kesting, R. Synthetic Polymer Membranes, 2nd Ed, Wiley-Interscience, 1985) or as a liquid membrane containing an ion exchanger (see for example Ion Exchange Processes : Advances and Applications, A. Dyer, M. J. Hudson, P. A. Williams.(Eds.) Royal Society of Chemistry, 1993). Both types facilitate the transfer of an ion across the membrane in exchange for a counter-flow of another ion. For example, quaternary ammonium salts in liquid membranes will facilitate the exchange of chloride ions flowing in one direction across the membrane with a flow of bromide ions moving in the opposite direction.

For the purposes of this invention, the membrane can be formed in a number of ways. One way, is as a supported liquid membrane (SLM) (see Liquid Membranes: Theory and applications, Noble, R. D and Way, J. D (Eds.) ACS Symposium Series 347, American Chemical Society, 1987). In such membranes a porous support polymer contains a solvent imbibed in the pores. An ion-exchanger is dissolved in the solvent thereby creating the SLM. A related SLM is a solvent-polymer membrane in which the solvent plus ion exchanger acts as a plasticizer for a polymer. For example a poly(vinyl chloride) film containing a phthalate plasticizer and an ion exchanger can create an ion exchange membrane. A third type of ion exchange membrane can be formed by modification of a polymer backbone to incorporate ion exchange groups directly linked to the polymer. Films of such materials can be cast or fabricated in a form suitable for this invention.

BRIEF DESCRIPTION OF THE DRAWINGS

FIG. 1. Is a graphical representation of the processes embodied in the current invention. It presents an idealized oxygen sensor and shows how the ion exchange membrane would keep the interior electrolyte replenished from the environment.

DETAILED DESCRIPTION OF THE INVENTION

Although the performance of many gas sensors can be improved using the principles outlined in this invention, the description of the invention will focus on a sensor for dissolved oxygen. A Clark cell for this system consists of a inert cathode, typically gold or platinum, and a reversible anode such as silver/silver chloride. Oxygen reduction at the cathode produces hydroxide ions that build up in the vicinity of the cathode. As current flows, there is a concomitant depletion of chloride ions in the vicinity of the anode. These concentration changes alter the stability of the sensor, and as the electrolyte is consumed, will ultimately inactivate the sensor. FIG. 1 shows, in diagrammatic form, how the invention alleviates these problems. This problem has been central to Clark cells since their inception and is mentioned as a problem in many earlier patents (See U.S. Pat. No. 5,212,050).

The invention describes an anion exchanger within the membrane which is capable of removing the hydroxide ions produced and capable as well of supplying the required chloride ions to the inside of the cell. The external solution being analyzed acts as a sink for hydroxide ions and a source of chloride ions in this system. For example, dissolved oxygen in seawater could be analyzed with such a device. The invention will ensure a longer working lifetime and greater stability of the sensor over time, when measured against sensors produced by the current state of the art with equivalent electrolyte volumes. The medium in which the gas is being measured need only have sufficient chloride ions for the exchange mechanism to operate and sufficient capacity to absorb hydroxide ions, opening the analysis of dissolved gases to a wide range of possible substances, including foodstuffs and biological fluids.

For the oxygen sensors described above, the chemical nature of the anion exchanger is not critical provided that the rate of anion exchange is sufficient to maintain the electrolyte composition within the sensor. Suitable anion exchangers may include, but are not restricted to:

ammonium salts and quaternary ammonium salts (R1R2R3R4N$^+$X$^-$)

guanidinium salts (R1R2NC$^+$(NR3R4)NR5R6X$^-$)

cationic metal complexes (L$_n$M$^{m+}$X$^{m-}$)

other cationic anion exchangers where R, R1,R2,R3,R4,R5,R6 are hydrogen, alkyl, aryl, or other groups sufficient to create a high affinity of the exchanger for the membrane phase, X$^-$ is an anion such as chloride, bromide, acetate etc., and L is a ligand for the metal M$^{m+}$ such that the complex has a high affinity for the membrane phase.

One preferred version of an oxygen sensor using this invention is based on a SLM fabricated from a microporous Teflon membrane with a high-boiling solvent such as ortho-nitrophenyl octyl ether or dioctyl adipate imbibed in the pores. A related version uses a high molecular weight poly(vinyl chloride) plasticized with ortho-nitrophenyl octyl ether or dioctyl adipate. The membrane is cast from a solution of the polymer and plasticizer in a volatile solvent such as tetrahydrofuran or trifluroethanol. Either type of membrane can be fabricated with 1–5 wt % of added anion exchanger preferably drawn from the list of types disclosed above.

A preferable embodiment of the invention is to form the ion exchange membrane so as to be a "thin film". By this means the response of a sensor using such a membrane can be significantly improved. The effect of "thin" membranes on sensor performance has been discussed frequently in the patent literature (For example, see U.S. Pat. No. 4,409,980).

Membranes such as those described by the invention can be applied to form an amperometric sensor with a large number of geometries and construction methods. The invention is capable of being applied in place of existing gas permeable membranes which otherwise lack the ion exchange capability to improve the lifetime and stability of an existing sensor. The invention can also be applied to "solid state" micro-fabricated sensor systems to more fully take advantage of the low electrolyte volumes required. This could, for instance, take the form of a membrane cast in place over a suitable electrolyte for the oxygen sensor which has in turn been placed over a pair of electrodes so as to form a "solid state" sensor. Such a sensor would have the ability to be stored "dry" to be "wetted" before use (See U.S. Pat. No. 4,933,048). Other prior art pertaining to permeable polymeric membranes can be found in U.S. Pat. No. 4,534,356 where a bound electrolyte is discussed but does not include ion exchangers or the regulation of the internal electrolyte composition by such exchangers.

We claim:

1. A gas permeable supported liquid membrane comprising a guanidinium salt.

2. The membrane of claim 1 where the supported liquid membrane comprises a porous support polymer comprising a solvent.

3. The membrane of claim 2 where the porous support polymer is a polytetrafluoroethylene membrane and the solvent is selected from the group consisting of o-nitrophenyl octyl ether, and dioctyl adipate.

4. The membrane of claim 1 where the supported liquid membrane comprises a plasticized polymer.

5. The membrane of claim 4 where the plasticized polymer comprises poly(vinyl chloride) and a phthalate plasticizer.

6. The membrane of claim 4 where the plasticized polymer is high molecular weight poly(vinyl chloride) plasticized with a solvent selected from the group consisting of o-nitrophenyl octyl ether, dioctyl adipate, and mixtures thereof.

7. The membrane of claim 1 comprising from 1% to 5% of the guanidinium salt.

8. The membrane of claim 1 where the ir ditium salt has the formula [R$_1$R$_2$NC$^+$(NR$_3$R$_4$)NR$_5$R$_6$]X$^-$, where R$_1$, R$_2$, R$_3$, R$_4$, and R$_6$ are selected from the group consisting of hydrogen, alkyl, and aryl and X$^-$ is an anion.

9. An amperometric gas sensor, comprising:

a supported liquid membrane comprising a guanidinium salt.

10. The sensor of claim 9 where the sensor comprises an inert cathode, a reversible anode and a membrane.

11. The sensor of claim 9 further comprising an inert cathode and a reversible anode.

12. The sensor of claim 11 where the inert cathode comprises a material selected from the group consisig of gold arid platinum and the reversible anode is an Ag/AgCl electrode.

13. The sensor of claim 9 where the supported liquid membrane comprises a porous suapport polymer compriing a solvent.

14. The sensor of claim 9 where the supported liquid membrane comprises a plasticized polymer.

15. The sensor of claim 9 for sensing a gas selected from the group consisting of hydrogen sulfide, NO, CO, and oxygen.

16. The sensor of claim 15 where the gas is oxygen.

17. The sensor of claim 9 where the guanidinium salt removes a by-product of an electrode reaction.

18. The sensor of claim 17 where the by-product is hydroxide ion and the balancing electrolyte is chloride.

19. An amperometric gas sensor, comprising:

a supported liquid membrane comprising a guanidinium salt;

an electrolyte in contact with the supported liquid membrane at a first surface of the electrolyte; and a pair of electrodes in contact with a second, opposite surface of the electrolyte salt.

20. The sensor of claim 19 where the supported liquid membrane comprises a porous support polymer comrsing a solvent.

21. The sensor of claim 19 where the supported liquid mete copses a plasticized polymer.

* * * * *

UNITED STATES PATENT AND TRADEMARK OFFICE
CERTIFICATE OF CORRECTION

PATENT NO. : 6,391,174 B1
DATED : May 21, 2002
INVENTOR(S) : Rowe et al.

It is certified that error appears in the above-identified patent and that said Letters Patent is hereby corrected as shown below:

<u>Column 4,</u>
Line 27, "ir ditium" should read -- quanidinium --.
Line 39, "consisig" should read -- consisting --.
Line 40, "arid" should read -- and --.
Line 42, "suapport" should read -- support --.
Line 42, "compriing" should read -- comprising --.
Line 53, "ion and the balancing electrolyte is chloride." should read -- ion. --.
Line 60, "electrolyte salt." should read -- electrolyte --.
Line 62, "comrsing" should read -- comprising --.
Line 65, "mete copses" should read -- membrane comprises --.

Signed and Sealed this

Twenty-first Day of June, 2005

JON W. DUDAS
*Director of the United States Patent and Trademark Office*